(12) United States Patent
Sumiyoshi et al.

(10) Patent No.: US 8,404,274 B2
(45) Date of Patent: Mar. 26, 2013

(54) ASEPTIC COMBINATION PREPARATION

(75) Inventors: Nobuaki Sumiyoshi, Naruto (JP); Yasuhiro Mitsumoto, Naruto (JP); Shigeaki Arita, Itano-gun (JP); Seiji Tani, Tokushima (JP); Masaru Kobayashi, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 537 days.

(21) Appl. No.: 10/559,373

(22) PCT Filed: Jun. 4, 2004

(86) PCT No.: PCT/JP2004/007818
§ 371 (c)(1),
(2), (4) Date: Feb. 7, 2006

(87) PCT Pub. No.: WO2004/108059
PCT Pub. Date: Dec. 16, 2004

(65) Prior Publication Data
US 2006/0154873 A1 Jul. 13, 2006

(30) Foreign Application Priority Data
Jun. 6, 2003 (JP) .................................. 2003-163013

(51) Int. Cl.
*A61K 9/66* (2006.01)
*A61K 9/50* (2006.01)
*A61K 31/70* (2006.01)

(52) U.S. Cl. ........................... 424/455; 424/493; 514/23

(58) Field of Classification Search .................. None
See application file for complete search history.

(56) References Cited

U.S. PATENT DOCUMENTS

| 4,489,097 A * | 12/1984 | Stone ............................. 514/558 |
| 4,630,727 A | 12/1986 | Feriani et al. |
| 5,200,200 A | 4/1993 | Veech |
| 5,383,324 A * | 1/1995 | Segers et al. ..................... 53/425 |
| 5,871,477 A | 2/1999 | Isono et al. |
| 6,129,925 A * | 10/2000 | Kido et al. ..................... 424/400 |
| 6,572,603 B1 | 6/2003 | Tani et al. |
| 6,867,193 B1 * | 3/2005 | Nakamura et al. .............. 514/21 |

FOREIGN PATENT DOCUMENTS

| EP | 0 776 649 | 6/1997 |
| EP | 1 053 737 | 11/2000 |
| JP | 64-29262 | 1/1989 |
| JP | 6-105905 | 4/1994 |
| JP | 7-41071 | 5/1995 |
| JP | 9-87182 | 3/1997 |
| JP | 2003-88582 | 3/2003 |
| JP | 2004-154558 | 6/2004 |
| WO | 01/89478 | 11/2001 |

OTHER PUBLICATIONS

Panter-Brick (Europ. J. Intensive Care Medicine 2, 45-51, 1976) Intravenous Nutrition of babies and infants.*
Li et al. (Pharmaceutical Research 1993, 10, 535-541) A method for the early evaluation of . . .*
Yawara Yoshitoshi et al., "Basis for Infusions and Disease-Specific Infusions", Kyowa Kikaku Ltd., Mar. 31, 1990, pp. 334-336, with partial English translation.

* cited by examiner

*Primary Examiner* — David J Blanchard
*Assistant Examiner* — Tigabu Kassa
(74) *Attorney, Agent, or Firm* — Wenderoth, Lind & Ponack, L.L.P.

(57) ABSTRACT

There is provided an aseptic combination preparation to be mixed at the time of use, characterized in that the same medicinal ingredients are divided and preserved in two or more chambers. The aseptic combination preparations according to the present invention are a mixing type at the time of their use and are useful as infusions, various dialysis fluids, intraocular perfusion/washing solutions, coronary perfusion solutions, myocardial protective solutions, peritoneal lavage solutions, solutions for organ preservations, etc., which can eliminate adverse effects caused by medical error on a living body.

4 Claims, 1 Drawing Sheet

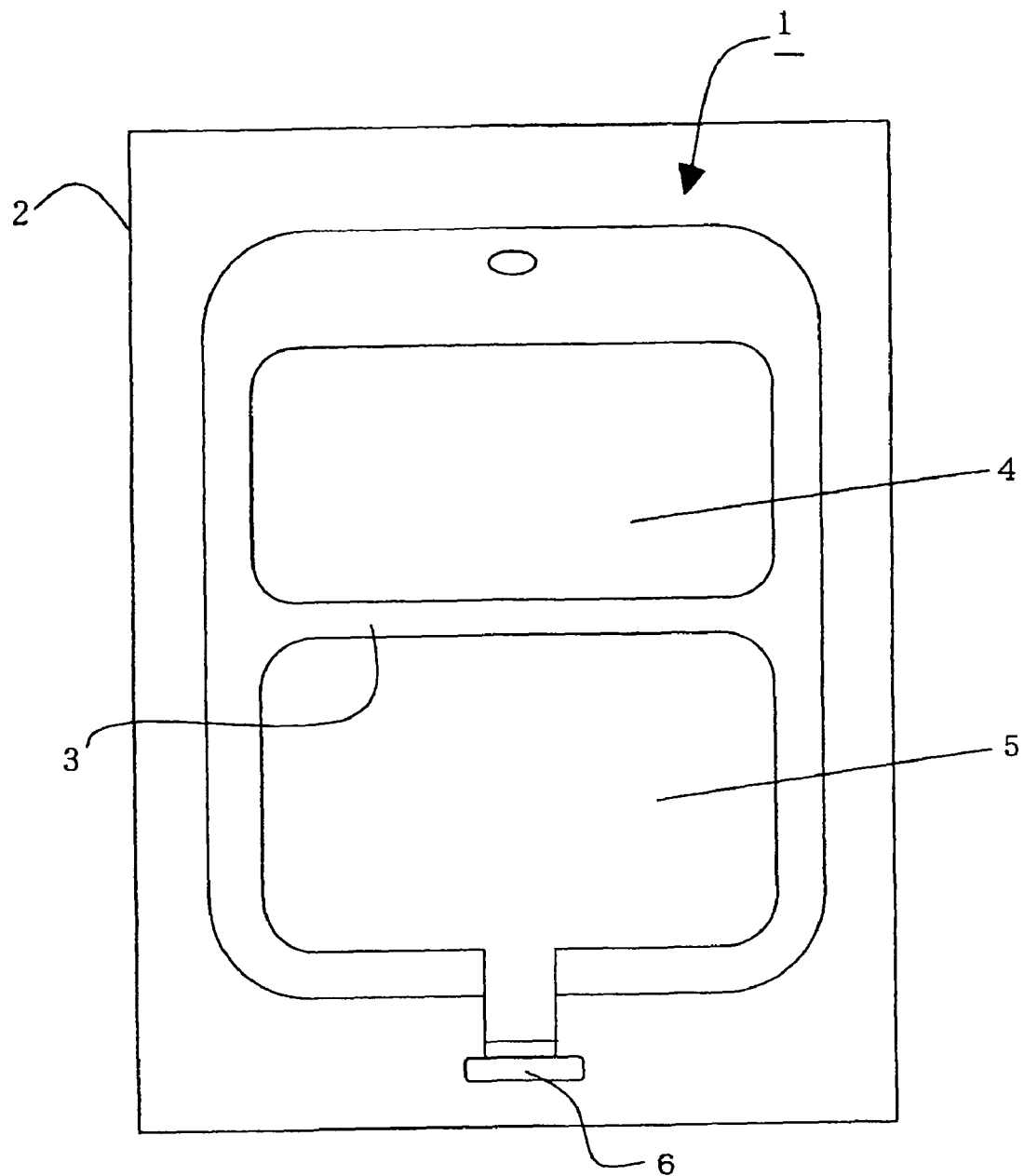

ASEPTIC COMBINATION PREPARATION

This application is a U.S. national stage of International Application No. PCT/JP2004/007818 filed Jun. 4, 2004.

TECHNICAL FIELD

The present invention relates to an aseptic combination preparation for medicinal ingredients to be separately preserved in a plurality of chambers, and to be mixed at the time of use, wherein the same medicinal ingredients are divided and accommodated in two or more chambers.

BACKGROUND ART

Intravenous hyperalimentation has been applied to patients who are impossible or insufficient in oral/enteral nutritional support. As an infusion preparation used thereupon, a sugar preparation, an amino acid preparation, an electrolyte preparation, a mixed vitamin preparation, a fat emulsion and the like are commercially available, and they are used by appropriate mixing in a hospital upon use, depending on the patient's conditions. However, such mixing and infusion procedures in the hospital are troublesome, and cause a problem of high possibility of bacterial pollution which is insanitary. Therefore, for example, an infusion container having a plurality of chambers which are divided by a partition wall has been developed, and used in hospitals. Further, some medicinal ingredients which are administered to a patient by intravenous injection cause an undesirable change with the lapse of time when mixed and dissolved in advance and thus are unstable. For example, when an amino acid-containing solution and a glucose-containing solution are accommodated and preserved in the same chamber, a mixed solution is browned through the so-called Maillard reaction. When a fat emulsion and an electrolyte solution are accommodated and preserved in the same chamber, fat components are aggregated. Further, when a carbonate-containing solution and a calcium salt-containing solution or a magnesium salt-containing solution are accommodated and preserved in the same chamber, a precipitate of calcium carbonate or magnesium carbonate is produced to cause an undesirable change. Such problem can be solved by storing medicinal ingredients separately in a plurality of chambers, mixing such ingredients immediately before administration, and administering the resulting mixture to a patient. For such problem, there has been developed a preparation comprising a plurality of chambers for accommodating and storing medicinal ingredients which are undesirable when mixed in advance, in different chambers. Examples of such preparation include SUB-LOOD-B (Fuso Pharmaceutical Industries, Ltd.) in which sodium bicarbonate is placed in a plastic container having a volume of 1 liter, and calcium chloride and magnesium chloride are placed in a glass vial having a volume of 10 milliliter, and Aminotripa (Otsuka Pharmaceutical Co., Ltd.) in which an amino acid and a sugar solution are separated and accommodated in different chambers of a plastic container having a plurality of chambers divided by a partition wall.

Like this, previously, medicinal ingredients which are not desirable when mixed in advance are separated and preserved in different chambers, these medicinal ingredients are mixed immediately before administration, and the mixture is administered to a patient. As an infusion container used in this kind of administration, for example, there is a container in which a plurality of chambers for dividing and accommodating medicinal ingredients are formed in a container body made of a synthetic resin film (for example, Patent Literature 1). The aforementioned infusion container has an advantage that a plurality of medicinal ingredients can be isolated and preserved, and at the time of use, they can be easily mixed and dissolved under sterile conditions by communication through a partition wall. However, there may cause a mistake that this communicating operation is forgotten, resulting in only one of medicinal ingredients is administered to a patient. When medicinal ingredients separated and preserved in different chambers are properly mixed, and are administered to a patient, for example, a potassium ion concentration, an osmotic pressure ratio and others of a medicinal ingredient-containing solution after mixing are set in the range suitable for administration, but in the case where only one of solutions is administered to a patient by the aforementioned mistake, the life of a patient is threatened in some cases. For example, in the case of an infusion preparation in which a medicinal ingredient-containing a potassium ion as an electrolyte at a high concentration is accommodated in one chamber of a plurality of chambers, the mistake of forgetting communication operation results in the administration of only the medicinal ingredient (potassium ion of high concentration) to a patient. When the potassium ion concentration is excessively high, a patient develops hyperkalemia and, in the worst case, the patient may be led to death by cardiac arrest. In addition, when an osmotic pressure ratio of a medicinal ingredient-containing solution divided and accommodated in one chamber of a plurality of chambers is excessively high or low, and if operation of chamber communicating, followed by mixing the medicinal ingredients, is forgotten, such mistake of administration of only the medicinal ingredient solution to a patient causes serious condition in patients as a result from severe vessel pain and destruction of erythrocytes in the blood. Accordingly, an aseptic combination preparation which solves the above problems and eliminates adverse effects caused by medical error on a living body has been desired in the medical fields.

Patent Literature 1: JP-A No. 2002-136570

DISCLOSURE OF THE INVENTION

An object of the present invention is to provide an aseptic combination preparation which solves the above problems and eliminates adverse effects caused by medical error on a living body.

As a result of intensive studies on the aforementioned problems, the present inventors have found that an aseptic combination preparation characterized in that the medicinal ingredients are separated and preserved in a plurality of chambers, the said aseptic combination preparation is mixed at the time of use, and the same medicinal ingredients are divided and preserved in two or more chambers has been successfully produced. At the same time, the present inventors have found that the said preparation can solve at once the aforementioned problems present in the previously developed preparations, said problems being caused by forgetting to communicating operation between the chambers. The present inventors have further made studies, and completed the present invention.

That is, the present invention relates to:

(1) an aseptic combination preparation to be mixed at the time of use, wherein the same medicinal ingredients are divided and accommodated in two or more chambers, (2) the aseptic combination preparation according to the above (1), wherein a plurality of chambers are arranged in one container, or arranged separately in two or more containers, (3) the aseptic combination preparation according to the above (1) or (2), wherein an osmotic pressure ratio of each solution of medicinal ingredients divided and accommodated in a plurality of chambers is adjusted in the range of 0.5 to 8, (4) the aseptic combination preparation according to the above (3), wherein a bicarbonate salt and a sugar are divided and accommodated in a plurality of different chambers, respectively, (5) the aseptic combination preparation according to the above (3), wherein the same medicinal ingredients divided and accommodated in a plurality of chambers are a sodium salt or/and a sugar, (6) the aseptic combination preparation according to the above (1) or (2), wherein potassium ion concentration in each medicinal ingredient-containing solution divided and accommodated in a plurality of chambers is adjusted to not higher than 40 mEq/L, (7) the aseptic combination preparation according to the above (6), wherein the same medicinal ingredients divided and accommodated in a plurality of chambers are a potassium salt, and (8) the aseptic combination preparation according to any one of the above (1) to (7), wherein the container is a plastic container in which the partition wall of a plurality of chambers can be communicated at the time of use, and thus medicinal ingredients can be aseptically mixed.

Effect of the Invention

Since in the aseptic combination preparations of the present invention, osmotic pressure ratio and potassium ion concentration of each medicinal solution to be accommodated in a plurality of chambers are adjusted in a proper range, and there is no risk of causing hemolysis due to low osmotic pressure, and hyperkalemia, etc., the present preparations can inhibit adverse effects on a living body by medical error even if the medicinal solution in only one chamber is administered to a patient by mistake.

BRIEF DESCRIPTION OF THE DRAWINGS

FIG. 1 shows a plane view of a gas permeable plastic container used in one embodiment of aseptic combination preparations of the present invention.

EXPLANATION OF SYMBOLS

1 Plastic container
2 Exterior bag
3 Partition wall (communication part)
4 Chamber A wherein medicinal ingredients-containing solution is preserved.
5 Chamber B wherein medicinal ingredients-containing solution is preserved.
6 Outlet of medicinal ingredients-containing solution to be administered.

BEST MODE FOR CARRYING OUT THE INVENTION

Embodiments of the present invention will be explained below.

An aseptic combination preparation according to the present invention is characterized in that medicinal ingredients are divided and preserved in a plurality of chambers as a medicinal solution, such ingredients are mixed at the time of use, and the same medicinal ingredients are divided and preserved in two or more chambers. In the present invention, "divided and preserved in a plurality of chambers" means that a plurality of chambers are arranged in one container, and medicinal ingredients may be divided and preserved in each chamber of the container, or a plurality of chambers are arranged separately in two or more containers, and medicinal ingredients may be divided and preserved in the two or more containers. When a plurality of chambers are arranged separately in two or more containers, materials and forms of such containers are not particularly limited, but the known ones may be used. Specifically, examples of such containers include a glass ample, a glass vial, a glass bottle, a plastic ample, a plastic bottle and a plastic bag, and a combination of two or more containers selected from these containers may be used. It is enough that medicinal ingredients divided and accommodated in selected two or more containers are mixed at the time of their use. For example, there is a case where the containers are connected with a thin tube, and medicinal ingredients divided and accommodated in the container are mixed by pressing the thin tube, etc. so as to administer the medicinal ingredients to a patient.

In addition, when a plurality of chambers are arranged in one container, preferable examples include a container in which two or more chambers of the container are divided by a partition wall (communication part), and one chamber of the container is communicated with an adjacent other chamber by pressing the one chamber from outside. Further examples include a chamber having a structure in which a breakable passage closing body is provided in a partition wall for comparting the container into two or more chambers. Preferable examples of such containers include containers described, for example, in JP-A-06-105905, JP-A-06-286087, JP-B-07-41071, JP-A-07-155361, JP-A-08-215287, and JP-A-2002-080048.

The aseptic combination preparation of the present invention is characterized in that the same medicinal ingredients are divided and accommodated in two or more chambers, wherein a medicinal solution containing medicinal ingredients are separated and preserved in the aforementioned a plurality of chambers which are arranged separately in two or more containers, or a plurality of chambers arranged in one container which is divided by a partition wall, and they are mixed at the time of use. Further, it is characterized in that the same medicinal ingredients divided and accommodated in two or more chambers is a potassium salt, a sodium salt or a sugar. In this case, one or more compounds selected from a potassium salt, a sodium salt and a sugar may be divided and accommodated in the same chamber. By doing like this, the aforementioned adverse effect on a living body by medical mistake can be eliminated. In the present invention, the medicinal ingredient refers to a composition component such as infusions conventionally used, various dialysis fluids, intraocular perfusion/washing solutions, coronary perfusion solutions, myocardial protective solutions, peritoneal lavage solutions, solutions for organ preservation, etc., and in particular, electrolytes and sugars.

In the present invention, as a sodium salt in a liquid preparation constituting a medicinal ingredient-containing solution, the known compounds can be used, and examples of such compounds include sodium chloride, sodium dihydrogen phosphate, disodium hydrogen phosphate, sodium sulfate, trisodium citrate, sodium acetate, borax and sodium lactate. The sodium salt may be in a form of a hydrate (e.g. hemihydrate, monohydrate, dihydrate, trihydrate, tetrahydrate, hexahydrate, etc.). These sodium salts can be usually dissolved in distilled water for injection to obtain a liquid preparation, preferably an aqueous solution.

In the present invention, as a sugar which is used in a medicinal ingredient-containing solution, sugars which have been used conventionally in various infusions may be used. For example, it is preferred to use a reducing sugar such as glucose, fructose and maltose. In particular, from a viewpoint of blood sugar management, it is preferable to use glucose. Two or more kinds of these reducing sugars may be used by mixing them, or a mixture obtained by adding sorbitol, xylitol, or glycerin to these reducing sugars may be used. As a solvent for the sugar, distilled water for injection is usually used. The known carbohydrate infusion may be used. The aforementioned sodium salt and sugar may be divided and accommodated in two or more same chambers of a plurality of chambers which are arranged separately in two or more containers, or two or more same chambers of a plurality of chambers which are arranged in one container divided by a partition wall which can communicate, or the sodium salt and sugar may be divided and accommodated in two or more chambers of these a plurality of chambers separately.

In the present invention, a medicinal ingredient-containing liquid preparation to be divided and accommodated in two or more chambers is suitably divided so as to be in the range of an osmotic pressure ratio of about 0.5 to 8, preferably about 1 to 5, more preferably about 1 to 3.

In the present invention, as a potassium salt in a liquid preparation constituting a medicinal ingredient-containing solution, the known compounds can be used, and examples of such compounds include potassium chloride, potassium acetate, potassium citrate, potassium dihydrogen phosphate, dipotassium hydrogen phosphate, potassium glycerophosphate, potassium sulfate, and potassium lactate. The potassium ion concentration in a liquid preparation constituting a medicinal ingredient-containing solution is usually not higher than about 40 mEq/L, preferably about 2 mEq/L to 40 mEq/L. The potassium salt may be in the form of a hydrate (e.g. hemihydrate, monohydrate, dehydrate, trihydrate, tetrahydrate, hexahydrate etc.). The potassium salt can be usually dissolved, for example, in distilled water for injection to obtain a liquid preparation, preferably an aqueous solution.

The aseptic combination preparation of the present invention can contain a bicarbonate salt in a different chamber from a chamber in which a sugar is contained. Examples of the bicarbonate salts include sodium hydrogen carbonate. As a solvent for the bicarbonate salt, distilled water for injection is usually used. The aforementioned same medicinal ingredients are divided in both chambers of a solution containing a bicarbonate salt and a solution containing a sugar, and the solutions in the chamber are adjusted to the above osmotic pressure ratio or/and potassium ion concentration.

The aseptic combination preparation of the present invention may contain an amino acid in a different chamber from a chamber in which a sugar is contained. Examples of the amino acids used include L-leucine, L-isoleucine, L-valine, L-lysine hydrochloride, L-threonine, L-tryptophan, L-methionine, L-phenylalanine, L-cysteine, L-tyrosine, L-arginine, L-histidine, L-alanine, L-proline, L-serine, glycine, L-aspartic acid, and L-glutamic acid. It is preferable that each amino acid used is a pure crystalline amino acid as in a general amino acid infusion. These amino acids usually need not to be a free amino acid, and may be used in the form of a pharmacologically acceptable salt, an ester, an N-acyl derivative, a salt of two kinds of amino acids, or a peptide. As a solvent for such amino acids, distilled water for injection is usually used. The previously known amino acid infusion may be used. Also in this case, the aforementioned same medicinal ingredients are divided in both chambers of a solution containing an amino acid and a solution containing a sugar, and both solutions are adjusted to the aforementioned osmotic pressure ratio or/and potassium ion concentration.

The aseptic combination preparation of the present invention may further contain vitamins. For example, vitamins may be dissolved and accommodated in one or two or more chambers of a plurality of chambers which are arranged separately in two or more containers, or one or two or more chambers of a plurality of chambers which are arranged in one container. Further, alternatively, a container for vitamin accommodation is arranged, and vitamins may be accommodated therein. The container for such vitamins is preferably such that a chamber accommodating vitamins is communicable with other chambers by pressing from outside. As the means, the above means known in the art may be used. In addition, the above same medicinal ingredients are appropriately divided in an aqueous solution of a container for vitamin accommodation, and the solutions are adjusted to the above osmotic pressure ratio and potassium ion concentration.

A vitamin solution filled in the aforementioned container for vitamin accommodation may be the known one. Specifically, there can be exemplified the case where a fat-soluble vitamin solution is filled in the aforementioned container for vitamin accommodation. Examples of such fat-soluble vitamins include vitamin A, vitamin D and vitamin E, and if desired, vitamin K may be blended. Examples of vitamin A include an ester form such as palmitic acid ester and acetic acid ester. Examples of vitamin D include vitamin $D_1$, vitamin $D_2$, vitamin $D_3$ (cholecalciferol) and an activated form thereof (hydroxy derivatives). Examples of vitamin E (tocopherol) include an ester form such as acetic acid ester and succinic acid ester. Examples of vitamin K (phytonadione) include derivatives such as phytonadione, menatetrenone, and menadione.

The above vitamins may be contained in a medicinal ingredient-containing solution accommodated in chamber A (numeral 4 in FIG. 1) or in a medicinal ingredient-containing solution accommodated in chamber B (numeral 5 in FIG. 1) wherein a medicinal ingredient constituting a solution containing said medicinal ingredients to be administered is divided and accommodated, though there is no particular limitation on the accommodation container for vitamins.

It goes without saying that stabilizers or pH adjusting agents may be appropriately used in the production of a medicinal ingredient-containing solution. Examples of the stabilizers include sodium hydrogen sulfite, sodium hydrogen pyrosulfite, sodium thiosulfate, sodium edetate and ethylenediamine. As the pH adjusting agent, a base or an acid can be used. Examples of the bases include inorganic bases such as sodium hydroxide, and potassium hydroxide. Examples of the acids include inorganic acids such as hydrochloric acid, and organic acids such as succinic acid, acetic acid, and citric acid, and particularly, organic acids are preferable.

With respect to the aseptic combination preparation of the present invention, for example, filling and accommodation of the medicinal ingredient-containing solution into a chamber of the container can be performed according to the conventional method, and examples of such method include a method of filling a medicinal ingredient-containing solution into each chamber under the inert gas atmosphere, closing the chamber with a stopper, and performing heat sterilization. Herein, for heat-sterilization, the known method such as high pressure steam sterilization and hot water shower sterilization can be adopted. If necessary, sterilization can be performed in an inert gas atmosphere such as carbon dioxide, nitrogen, and helium gases.

In the aseptic combination preparation of the present invention, when a plurality of chambers are arranged separately in two or more containers, at least one container among a plurality of containers accommodating medicinal ingredients may be a glass container.

In addition, in the aseptic combination preparation of the present invention, when a plurality of chambers are arranged in one container, for example, a plastic container in which a chamber accommodating a medicinal ingredients is preferably permitted to communicate with each other, the partition walls of a plurality of chambers in the container can be communicated at the time of use, and medicinal ingredients can be aseptically mixed.

Materials for forming each chamber in a plastic container having a plurality of communicable chambers may be resins having no problem of stability of medicinal ingredients to be preserved. With regard to the part which forms the chambers having a relatively large volume, there can be used flexible thermoplastic resins such as flexible polypropylene or a copolymer thereof; polyethylene or/and a copolymer thereof; polyvinyl acetate; partially saponified polyvinyl alcohol; a mixture of polypropylene and polyethylene or polybutene; olefin resins such as ethylene-propylene copolymer; partially crosslinked polyolefin; stylene-based elastomers; polyesters such as polyethylene terephthalate; flexible vinyl chloride resins; appropriately mixed materials therewith; and sheets formed in multilayer with the above materials including other materials such as nylon.

Further, in any aseptic combination preparation of the case where a plurality of chambers are arranged in one container, or the case where a plurality of chambers are arranged separately in two or more containers, a medicinal ingredient is divided and accommodated in chambers of the container. For example, in order to surely prevent denaturation or oxidation of a medicinal ingredient-containing solution, a container can be packaged with a gas barrier outer bag together with a deoxidizer. Inter alia, in the case where a plurality of chambers are arranged in one container and, for example, the partition walls of a plurality of chambers in a container are formed with easily peelable seal, this container is preferably enclosed in a gas barrier outer packaging bag in the state where an easily-peelable seal part is folded into two parts (folded state), so that the partition wall is not communicated by an external pressure. In addition, if necessary, the aforementioned inert gas filling packaging may be performed.

As a material for the outer packaging bag with gas barrier property, films and sheets of various materials which are generally used widely can be used. Examples of such materials include an ethylene/vinyl alcohol copolymer, polyvinylidene chloride, polyacrylonitrile, polyvinyl alcohol, polyamide, polyester, and films and sheets composed of a material containing at least one kind of them.

A deoxidizer which is enclosed in a space part between the outer bag and the container may be used, and there can be used, as the deoxidizer, (1) a material wherein iron carbide, iron carbonyl compound, iron oxide, iron powder, iron hydroxide or silicon iron, is coated with a metal halide, (2) a mixture of a dithionite; and (a) an alkaline earth metal hydroxide or an alkaline earth metal carbonate, (b) active carbon and water, (c) a compound having water of crystallization, (d) an alkaline substance or (d) an alcohol compound, (3) a mixture of an alkaline earth metal sulfite; and (a) an iron (II) compound, (b) a transition metal salt, (c) an aluminum salt, (d) an alkali compound containing an alkali metal or an alkaline earth metal, (e) an alkali compound containing nitrogen or (f) an ammonium salt and, (4) a mixture of (a) iron or zinc; and sodium sulfate monohydrate; or (b) a mixture of iron or zinc; sodium sulfate monohydrate; and a metal halide, (5) a mixture of iron, copper, tin, zinc or nickel; sodium sulfate heptahydrate or decahydrate; and a metal halide, (6) a mixture of a transition metal of the fourth period in the periodic table; tin or antimony; and water, or a mixture of a transition metal of the fourth period in the periodic table; tin or antimony; water; and a metal halide, and (7) a mixture of an alkali metal sulfite, ammonium sulfite, an alkali metal hydrogen sulfite, ammonium hydrogen sulfite, an alkali metal pyrosulfite or ammonium pyrosulfite; a transition metal salt or an aluminum salt; and water, and the like. In the present invention, a deoxidizer can be optionally selected appropriately from these known substances. Alternatively, as a deoxidizer, a commercially available deoxidizer can be used. Examples of such commercially available deoxidizers include "AGELESS" (manufactured by Mitsubishi Gas Chemical Company, Inc.), "MODURAN" (manufactured by Nippon Kayaku Co., Ltd.), "SEQUL" (manufactured by Nippon Soda Co., Ltd.), and "TAMOTSU" (manufactured by Oji Kako Co., Ltd.). The deoxidizer, when it is powdery, is preferably used by placing into an appropriate breathable small bag. It is preferable to use the deoxidizer which is put into a small pouch having a proper gas permeability, if the deoxidizer is in the form of a powder. When the oxidizer is a tablet, it may be used as it is without packaging.

The aseptic combination preparation of the present invention is useful, for example, as an antidote, an artificial kidney dialysis fluid, a peritoneal dialysis solution, an infusion, a root canal-enlarging agent (dental), an artificial cerebrospinal fluid, an intraocular perfusing solution, a coronary perfusion solution, a myocardial protective solution, a peritoneal lavage solution, or a solution for organ preservations. In addition, the process of the present invention can be utilized in a process for preparing the aforementioned various medicinal solutions.

The present invention will be explained in more detail below by way of Examples, but it should be understood that the present invention is not limited to these Examples.

EXAMPLES

Example 1

0.09 g of calcium chloride, 0.11 g of magnesium chloride, 1.20 g of sodium chloride and 0.31 g of glucose were dissolved in distilled water for injection to a total volume of 150 mL, thereby to obtain a glucose solution (referred to as solution X). Then, 0.97 g of sodium bicarbonate, 0.08 g of potassium dihydrogen phosphate, 2.38 g of sodium chloride and 0.07 g of potassium chloride were dissolved in distilled water for injection to a total volume of 350 mL, there by to obtain a solution (referred to as solution Y). After the solution X and the solution Y were respectively filtrated by the conventional method, 150 mL of solution X and 350 mL of solution Y were filled respectively in chamber A (numeral 4 in FIG. 1) for storage of medicinal ingredients-containing solution and chamber B (5 in FIG. 1) for storage of medicinal ingredients-containing solution in a gas-permeable plastic container (FIG. 1), wherein the partition wall of the chambers can be opened when used, the solutions in chamber A and chamber B can be mixed aseptically, and then the container was closed. The container filled with the solution X and the solution Y was heat-sterilized by the conventional method, followed by the secondary packaging (numeral 2 in FIG. 1) with a gas barrier film, thereby to obtain an aseptic combination preparation.

Comparative Example 1

0.09 g of calcium chloride, 0.11 g of magnesium chloride and 0.31 g of glucose were dissolved in distilled water for injection to a total volume of 150 mL, thereby to obtain a glucose solution (referred to as solution X). Then, 0.97 g of sodium bicarbonate, 0.08 g of potassium dihydrogen phosphate, 3.58 g of sodium chloride and 0.07 g of potassium chloride were dissolved in distilled water for injection to a total volume of 350 mL, thereby to obtain a solution (referred to as solution Y). After these solutions X and Y were filtered respectively by the conventional method, 150 mL of solution X and 350 mL of solution Y were filled respectively into chamber A for storage of medicinal ingredients-containing solution (numeral 4 in FIG. 1) and chamber B for storage of medicinal ingredients-containing solution (numeral 5 in FIG. 1) in a gas-permeable plastic container (FIG. 1), wherein the partition wall of the chambers can be opened when used and the solutions in chamber A and chamber B can be mixed aseptically, and then the both chambers were closed. The container filled with the solution X and the solution Y was heat-sterilized by the conventional method, followed by the secondary packaging with a gas barrier film, thereby to obtain an aseptic combination preparation.

With regard to the aseptic combination preparations prepared in Example 1 and Comparative Example 1, in one week after preparation, the solution X and the solution Y in chamber A for storage of medicinal ingredients-containing solution (numeral 4 in FIG. 1) and chamber B for storage of medicinal ingredients-containing solution (numeral 5 in FIG. 1) in each container were mixed respectively. Each of the solution X and the solution Y of Example 1 before mixing, the solution X and the solution Y of Comparative Example 1 before mixing, a mixed solution of the solution X and the solution Y of Example 1, and a mixed solution of the solution X and the solution Y of Comparative Example 1 was measured for an osmotic pressure ratio, and the results are shown in Table 1. The osmotic pressure ratio was measured based on the Japanese Pharmacopoeia, the fourteenth edition, general tests: measurement of osmotic pressure.

TABLE 1

| | | | Example 1 | | Comparative Example 1 | |
|---|---|---|---|---|---|---|
| Solution X | Formulation (150 ml) | Calcium chloride | 0.09 g | Calcium chloride | 0.09 g | |
| | | Magnesium chloride | 0.11 g | Magnesium chloride | 0.11 g | |
| | | Glucose | 0.31 g | Glucose | 0.31 g | |
| | | Sodium chloride | 1.20 g | | | |
| | Osmotic pressure ratio * | | 1.0 | | 0.1 | |
| Solution Y | Formulation (350 ml) | Sodium hydrogen carbonate | 0.97 g | Sodium hydrogen carbonate | 0.97 g | |
| | | Potassium dihydrogen phosphate | 0.08 g | Potassium dihydrogen phosphate | 0.08 g | |
| | | Sodium chloride | 2.38 g | Sodium chloride | 3.58 g | |
| | | Potassium chloride | 0.07 g | Potassium chloride | 0.07 g | |
| | Osmotic pressure ratio * | | 1.0 | | 1.4 | |
| Mixed solution of X and Y | Formulation (500 ml) | Calcium chloride | 0.09 g | Calcium chloride | 0.09 g | |
| | | Magnesium chloride | 0.11 g | Magnesium chloride | 0.11 g | |
| | | Glucose | 0.31 g | Glucose | 0.31 g | |
| | | Sodium chloride | 0.97 g | Sodium chloride | 0.97 g | |
| | | Sodium hydrogen carbonate | | Sodium hydrogen carbonate | | |

TABLE 1-continued

| | | Example 1 | | Comparative Example 1 | |
|---|---|---|---|---|---|
| | Potassium dihydrogen phosphate | 0.08 g | Potassium dihydrogen phosphate | 0.08 g | |
| | Sodium chloride | 3.58 g | Sodium chloride | 3.58 g | |
| | Potassium chloride | 0.07 g | Potassium chloride | 0.07 g | |
| Osmotic pressure ratio * | | 1.0 | | 1.0 | |

(Note)
*: osmotic pressure ratio relative to physiological saline

Example 2

2.10 g of L-leucine, 1.20 g of L-isoleucine, 1.20 g of L-valine, 1.97 g of L-lysine hydrochloride, 0.86 g of L-threonine, 0.30 g of L-tryptophan, 0.59 g of L-methionine, 1.05 g of L-phenylalanine, 0.15 g of L-cysteine, 0.08 g of L-tyrosine, 1.58 g of L-arginine, 0.75 g of L-histidine, 1.20 g of L-alanine, 0.75 g of L-proline, 0.45 g of L-serine, 0.89 g of glycine, 0.15 g of L-aspartic acid, 0.15 g of L-glutamic acid, 0.46 g of dipotassium phosphate and 0.03 g of sodium hydrogen sulfite were dissolved in distilled water for injection to a total volume of 150 mL, thereby to obtain an amino acid solution (referred to as solution P). Then, 37.50 g of glucose, 0.40 g of sodium chloride, 1.15 g of 70% sodium lactate, 0.56 g of calcium gluconate, 0.31 g of magnesium sulfate, 0.0007 g of zinc sulfate, 0.015 g of sodium hydrogen sulfite, and 0.41 g of dipotassium phosphate were dissolved in distilled water for injection to a total volume of 350 mL, thereby to obtain a glucose solution (referred to as solution Q). Acetic acid was added to the resulting solution P and solution Q to adjust the pH to 6.9 and 5.0, respectively. After the solution P and the solution Q were filtered respectively by the conventional method, 150 mL of solution P and 350 mL of solution Q were filled respectively into chamber A for storage of medicinal ingredients-containing solution (numeral 4 in FIG. 1) and chamber B for storage of medicinal ingredients-containing solution (numeral 5 in FIG. 1) in a gas-permeable plastic container (FIG. 1), wherein the partition wall of the chambers can be opened when used and the solutions in chamber A and chamber B can be mixed aseptically, and then the both chambers were closed. The container filled with the solution P and the solution Q was heat-sterilized by the conventional method, followed by the secondary packaging with a gas barrier film, thereby to obtain an aseptic combination preparation.

Comparative Example 2

2.10 g of L-leucine, 1.20 g of L-isoleucine, 1.20 g of L-valine, 1.97 g of L-lysine hydrochloride, 0.86 g of L-threonine, 0.30 g of L-tryptophan, 0.59 g of L-methionine, 1.05 g of L-phenylalanine, 0.15 g of L-cysteine, 0.08 g of L-tyrosine, 1.58 g of L-arginine, 0.75 g of L-histidine, 1.20 g of L-alanine, 0.75 g of L-proline, 0.45 g of L-serine, 0.89 g of glycine, 0.15 g of L-aspartic acid, 0.15 g of L-glutamic acid, 0.87 g of dipotassium phosphate and 0.03 g of sodium hydrogen sulfite were dissolved in distilled water for injection to a total volume of 150 mL, thereby to obtain an amino acid solution (referred to as solution P). Then, 37.50 g of glucose, 0.40 g of sodium chloride, 1.15 g of 70% sodium lactate, 0.56 g of calcium gluconate, 0.31 g of magnesium sulfate, 0.0007 g of zinc sulfate, and 0.015 g of sodium hydrogen sulfite were dissolved in distilled water for injection to a total volume of 350 mL, thereby to obtain a glucose solution (referred to as solution Q). Acetic acid was added to the resulting solution P and solution Q to adjust the pH to 6.9 and 5.0, respectively. After the solution P and the solution Q were filtered respectively by the conventional method, 150 mL of solution P and 350 mL of solution Q were filled respectively into chamber A for storage of medicinal ingredients-containing solution (numeral 4 in FIG. 1) and chamber B for storage of medicinal ingredients-containing solution (numeral 5 in FIG. 1) in a gas-permeable plastic container (FIG. 1), wherein the partition wall of the chambers can be opened when used and the solutions in chamber A and chamber B can be mixed aseptically, and then the both chambers were closed. The container filled with the solution P and the solution Q was heat-sterilized by the conventional method, followed by the secondary packaging with a gas barrier film, thereby to obtain an aseptic combination preparation.

With regard to the aseptic combination preparations prepared in Example 2 and Comparative Example 2, in one week after preparation, the solution P and the solution Q in each chamber were mixed. Each of the solution P and the solution Q of Example 2 before mixing, the solution P and the solution Q of Comparative Example 2 before mixing, a mixed solution of the solution P and the solution Q of Example 2, and a mixed solution of the solution P and the solution Q of Comparative Example 2 was measured for potassium concentration, and each formulation and the results of potassium concentration are shown in Tables 2 to 4. The potassium concentration was measured based on the Japanese Pharmacopoeia, the fourteenth edition, general tests: liquid chromatography.

TABLE 2

| | Formulation (150 ml) | | Example 2 | | Comparative Example 2 | |
|---|---|---|---|---|---|---|
| Solution P | Composition component | L-leucine | 2.10 g | L-leucine | 2.10 g |
| | | L-isoleucine | 1.20 g | L-isoleucine | 1.20 g |
| | | L-valine | 1.20 g | L-valine | 1.20 g |
| | | L-lysine hydrochloride | 1.97 g | L-lysine hydrochloride | 1.97 g |
| | | L-threonine | 0.86 g | L-threonine | 0.86 g |
| | | L-tryptophan | 0.30 g | L-tryptophan | 0.30 g |
| | | L-methionine | 0.59 g | L-methionine | 0.59 g |
| | | L-phenylalanine | 1.05 g | L-phenylalanine | 1.05 g |
| | | L-cysteine | 0.15 g | L-cysteine | 0.15 g |
| | | L-tyrosine | 0.08 g | L-tyrosine | 0.08 g |
| | | L-arginine | 1.58 g | L-arginine | 1.58 g |
| | | L-histidine | 0.75 g | L-histidine | 0.75 g |
| | | L-alanine | 1.20 g | L-alanine | 1.20 g |
| | | L-proline | 0.75 g | L-proline | 0.75 g |
| | | L-serine | 0.45 g | L-serine | 0.45 g |
| | | Glycine | 0.89 g | Glycine | 0.89 g |
| | | L-aspartic acid | 0.15 g | L-aspartic acid | 0.15 g |
| | | L-glutamic acid | 0.15 g | L-glutamic acid | 0.15 g |
| | | Dipotassium phosphate | 0.46 g | Dipotassium phosphate | 0.87 g |
| | Stabilizer | Sodium hydrogen sulfite | 0.03 g | Sodium hydrogen sulfite | 0.03 g |
| | pH adjusting agent | Acetic acid | q.s. | Acetic acid | q.s. |
| | Potassium concentration | 35 mEq/L | | | |

TABLE 3

| | Formulation (350 ml) | | Example 2 | | Comparative Example 2 | |
|---|---|---|---|---|---|---|
| Solution Q | Composition component | Glucose | 37.50 g | Glucose | 37.50 g |
| | | Sodium chloride | 0.40 g | Sodium chloride | 0.40 g |
| | | 70% Sodium lactate | 1.15 g | 70% Sodium lactate | 1.15 g |
| | | Calcium gluconate | 0.56 g | Calcium gluconate | 0.56 g |
| | | Magnesium sulfate | 0.31 g | Magnesium sulfate | 0.31 g |
| | | Zinc sulfate | 0.0007 g | Zinc sulfate | 0.0007 g |
| | | Dipotassium phosphate | 0.41 g | | |
| | Stabilizer | Sodium hydrogen sulfite | 0.015 g | Sodium hydrogen sulfite | 0.015 g |
| | pH adjusting agent | Acetic acid | q.s. | Acetic acid | q.s. |
| | Potassium concentration | 13 mEq/L | | 0 mEq/L | |

TABLE 4

| | Formulation (500 ml) | | Example 2 | | Comparative Example 2 | |
|---|---|---|---|---|---|---|
| Mixture of solution P and solution Q | Composition component | L-leucine | 2.10 g | L-leucine | 2.10 g |
| | | L-isoleucine | 1.20 g | L-isoleucine | 1.20 g |
| | | L-valine | 1.20 g | L-valine | 1.20 g |
| | | L-lysine hydrochloride | 1.97 g | L-lysine hydrochloride | 1.97 g |
| | | L-threonine | 0.86 g | L-threonine | 0.86 g |
| | | L-tryptophan | 0.30 g | L-tryptophan | 0.30 g |

TABLE 4-continued

| Formulation (500 ml) | | Example 2 | | Comparative Example 2 | |
|---|---|---|---|---|---|
| | L-methionine | 0.59 g | L-methionine | 0.59 g |
| | L-phenylalanine | 1.05 g | L-phenylalanine | 1.05 g |
| | L-cysteine | 0.15 g | L-cysteine | 0.15 g |
| | L-tyrosine | 0.08 g | L-tyrosine | 0.08 g |
| | L-arginine | 1.58 g | L-arginine | 1.58 g |
| | L-histidine | 0.75 g | L-histidine | 0.75 g |
| | L-alanine | 1.20 g | L-alanine | 1.20 g |
| | L-proline | 0.75 g | L-proline | 0.75 g |
| | L-serine | 0.45 g | L-serine | 0.45 g |
| | Glycine | 0.89 g | Glycine | 0.89 g |
| | L-aspartic acid | 0.15 g | L-aspartic acid | 0.15 g |
| | L-glutamic acid | 0.15 g | L-glutamic acid | 0.15 g |
| | Dipotassium phosphate | 0.87 g | Dipotassium phosphate | 0.87 g |
| | Glucose | 37.50 g | Glucose | 37.50 g |
| | Sodium chloride | 0.40 g | Sodium chloride | 0.40 g |
| | 70% Sodium lactate | 1.15 g | 70% Sodium lactate | 1.15 g |
| | Calcium gluconate | 0.56 g | Calcium gluconate | 0.56 g |
| | Magnesium sulfate | 0.31 g | Magnesium sulfate | 0.31 g |
| | Zinc sulfate | 0.0007 g | Zinc sulfate | 0.0007 g |
| Stabilizer | Sodium hydrogen sulfite | 0.045 g | Sodium hydrogen sulfite | 0.045 g |
| pH adjusting agent | Acetic acid | q.s. | Acetic acid | q.s. |
| Potassium concentration | 13 mEq/L | | 13 mEq/L | |

Example 3

2.27 g of sodium chloride, 0.075 g of potassium chloride and 2.97 g of sodium bicarbonate were dissolved in distilled water for injection to a total volume of 500 mL, thereby to obtain a solution (referred to as solution X). Then, 3.90 g of sodium chloride, 0.075 g of potassium chloride, 0.02599 g of calcium chloride, 0.1027 g of magnesium chloride, 0.0414 g of anhydrous sodium acetate, 0.1800 g of glacial acetic acid and 1.01 g of glucose were dissolved in distilled water for injection to a total volume of 510 mL, thereby to obtain a solution (referred to as solution Y). After these solutions X and Y were filtered respectively by the conventional method, 500 mL of solution X and 510 mL of solution Y were filled respectively into chamber A for storage of medicinal ingredients-containing solution (numeral 4 in FIG. 1) and chamber B for storage of medicinal ingredients-containing solution (numeral 5 in FIG. 1) in a gas-permeable plastic container (FIG. 1), wherein the partition wall of the chambers can be opened when used and the solutions in chamber A and chamber B can be mixed aseptically, and then the both chambers were closed. The container filled with the solution X and the solution Y was heat-sterilized by the conventional method, followed by the secondary packaging (numeral 2 in FIG. 1) with a gas barrier film, thereby to obtain an aseptic combination preparation.

With regard to the aseptic combination preparations prepared in Example 3, in one week after preparation, the solution X and the solution Y in chamber A (numeral 4 in FIG. 1) for storage of medicinal ingredients-containing solution and chamber B (numeral 5 in FIG. 1) for storage of medicinal ingredients-containing solution in each container were mixed. Each of the solution X and the solution Y of Example 3 before mixing, and a mixed solution of the solution X and the solution Y of Example 3 was measured for an osmotic pressure ratio, and the results are shown in Tables 5 to 7. The osmotic pressure ratio was measured based on the Japanese Pharmacopoeia, the fourteenth edition, general tests: measurement of osmotic pressure.

TABLE 5

| | | Example 3 | |
|---|---|---|---|
| Solution X | Formulation (500 ml) | Sodium chloride | 2.27 g |
| | | Potassium chloride | 0.075 g |
| | | Sodium bicarbonate | 2.97 g |
| | Composition | | |
| | Na$^+$ | 148.4 mEq/L | |
| | K$^+$ | 2.0 mEq/L | |
| | Ca$^{2+}$ | — | |
| | Mg$^{2+}$ | — | |
| | Cl$^-$ | 79.7 mEq/L | |
| | HCO$_3^-$ | 70.7 mEq/L | |
| | Acetate | — | |
| | Glucose | — | |
| | Osmotic pressure ratio * | 1.1 | |

TABLE 6

| | | Example 3 | |
|---|---|---|---|
| Solution Y | Formulation (510 ml) | Sodium chloride | 3.90 g |
| | | Potassium chloride | 0.075 g |
| | | Calcium chloride | 0.02599 g |
| | | Magnesium chloride | 0.1027 g |
| | | Anhydrous sodium acetate | 0.0414 g |
| | | Glacial acetic acid | 0.1800 g |
| | | Glucose | 1.01 g |

TABLE 6-continued

Example 3

| Composition | | |
|---|---|---|
| Na$^+$ | 130.18 | mEq/L |
| K$^+$ | 2.0 | mEq/L |
| Ca$^{2+}$ | 6.9 | mEq/L |
| Mg$^{2+}$ | 2.0 | mEq/L |
| Cl$^-$ | 141.7 | mEq/L |
| HCO$_3^-$ | — | |
| Acetate | 6.9 | mEq/L |
| Glucose | 2.0 | g/L |
| Osmotic pressure ratio * | 1.0 | |

(Note)
*: osmotic pressure ratio relative to physiological saline

TABLE 7

Example 3

| | | | | |
|---|---|---|---|---|
| Mixture of solution X and solution Y | Formulation (1010 ml) | Sodium chloride | 6.17 | g |
| | | Potassium chloride | 0.15 | g |
| | | Sodium bicarbonate | 2.97 | g |
| | | Calcium chloride | 0.2599 | g |
| | | Magnesium chloride | 0.1027 | g |
| | | Anhydrous sodium acetate | 0.0414 | g |
| | | Glacial acetic acid | 0.18 | g |
| | | Glucose | 1.01 | g |
| | Composition | | | |
| | | Na$^+$ | 140.0 | mEq/L |
| | | K$^+$ | 2.0 | mEq/L |
| | | Ca$^{2+}$ | 3.5 | mEq/L |
| | | Mg$^{2+}$ | 1.0 | mEq/L |
| | | Cl$^-$ | 111.0 | mEq/L |
| | | HCO$_3^-$ | 35.0 | mEq/L |
| | | Acetate | 3.5 | mEq/L |
| | | Glucose | 1.0 | g/L |
| | | Osmotic pressure ratio * | 1.0 | |

(Note)
*: osmotic pressure ratio relative to physiological saline

Example 4

An ocular perfusing/washing agent was prepared based on the following methods.

The composition components of solution A (composition components: sodium chloride 2.3207 g, sodium acetate 0.3 g, sodium citrate 0.5002 g, calcium chloride 0.077 g, magnesium chloride 0.1001 g and sodium bicarbonate 1.0514 g) were dissolved in water for injection. The pH of the solution was adjusted with hydrochloric acid to 7.8. The total volume was adjusted to 350 mL to obtain a solution A. The osmotic pressure ratio of the solution A was 1.0.

The composition components of solution B (composition components: glucose 0.4601 g, sodium chloride 0.9946 g, sodium acetate 0.3 g, calcium chloride 0.077 g, potassium chloride 0.1896 g and oxyglutathione 1.092 g) were dissolved in water for injection. The pH of the solution was adjusted with hydrochloric acid and sodium hydroxide to 4.5. The total volume of the solution was adjusted to 150 mL to obtain a solution B. The osmotic pressure ratio of the solution B was 1.0. 350 mL of the solution A was filtered according to the conventional method, and filled in a lower chamber (numeral 4 in FIG. 1) of a soft bag container made from polyfilm having two upper and lower chambers (see FIG. 1), while 150 mL of the solution B was filtered according to the conventional method, and filled in an upper chamber (numeral 5 in FIG. 1). Then, both of the chambers were closed. The container was heat-sterilized by the conventional method, followed by the secondary packaging (numeral 2 in FIG. 1) with a gas barrier film, thereby to obtain an ocular perfusing/washing agent, wherein the partition wall of the chambers can be communicated, permitting to admix the medicinal ingredients aseptically.

INDUSTRIAL APPLICABILITY

In the administration of an aseptic combination preparation wherein medicinal ingredients are divided and preserved in a plurality of chambers and the said medicinal ingredients which are divided and preserved in each chamber can be mixed by communication with each chamber just before administration to a patient, there can be provided the aseptic combination preparation which can inhibit adverse effects on a living body caused by medical error resulting from failure of forgetting the communication with each chamber. Therefore, the aseptic combination preparation can be used as infusions wherein two or more kinds of solutions are mixed, various dialysis fluids, intraocular perfusion/washing solutions, coronary perfusion solutions, myocardial protective solutions, peritoneal lavage solutions, solutions for organ preservation, etc.

The invention claimed is:

1. An aseptic combination preparation to be mixed at the time of use by opening a partition wall which separates two or more chambers of a container,
   comprising
   a first solution consisting essentially of dipotassium hydrogen phosphate, glucose, sodium chloride, sodium lactate, calcium gluconate, magnesium sulfate and zinc sulfate in a first chamber and
   a second solution consisting essentially of dipotassium hydrogen phosphate and at least one amino acid selected from the group consisting of L-leucine, L-isoleucine, L-valine, L-lysine hydrochloride, L-threonine, L-tryptophan, L-methionine, L-phenylalanine, L-cysteine, L-tyrosine, L-arginine, L-histidine, L-alanine, L-proline, L-serine, glycine, L-aspartic acid and L-glutamic acid in a second chamber,
   wherein the first solution and the second solution each have a potassium ion concentration of about 13 to 35 mEq/L,
   with the proviso that each of the solutions does not contain a bicarbonate salt.

2. The aseptic combination preparation according to claim 1, wherein the container is a plastic container.

3. An aseptic combination preparation to be mixed at the time of use by opening a partition wall which separates two or more chambers of a container,
   comprising
   a first solution consisting of sodium chloride, glucose, calcium chloride and magnesium chloride in a first chamber and
   a second solution consisting of sodium chloride, sodium hydrogen carbonate, dipotassium hydrogen phosphate and potassium chloride in a second chamber,
   wherein the first solution and the second solution each have an osmotic pressure ratio of about 1 relative to physiological saline.

4. The aseptic combination preparation according to claim 3, wherein the container is a plastic container.

* * * * *